United States Patent
Imai

(10) Patent No.: US 10,335,802 B2
(45) Date of Patent: Jul. 2, 2019

(54) CENTRIFUGE AND SEGMENT HOLDER

(71) Applicant: TERUMO KABUSHIKI KAISHA, Tokyo (JP)

(72) Inventor: Tadashi Imai, Leuven (BE)

(73) Assignee: Terumo Kabushiki Kaisha, Tokyo (JP)

( * ) Notice: Subject to any disclaimer, the term of this patent is extended or adjusted under 35 U.S.C. 154(b) by 147 days.

(21) Appl. No.: 15/558,623

(22) PCT Filed: Mar. 17, 2016

(86) PCT No.: PCT/JP2016/058613
§ 371 (c)(1),
(2) Date: Sep. 15, 2017

(87) PCT Pub. No.: WO2016/148265
PCT Pub. Date: Sep. 22, 2016

(65) Prior Publication Data
US 2018/0085760 A1 Mar. 29, 2018

(30) Foreign Application Priority Data
Mar. 18, 2015 (JP) ................................. 2015-054160

(51) Int. Cl.
*B04B 5/04* (2006.01)
*B04B 5/02* (2006.01)
(Continued)

(52) U.S. Cl.
CPC .............. *B04B 5/02* (2013.01); *A61M 1/025* (2013.01); *A61M 1/0272* (2013.01);
(Continued)

(58) Field of Classification Search
CPC ....... B04B 5/02; B04B 5/0421; B04B 5/0442; B04B 5/0428; B04B 2005/0435; A61M 1/025; A61M 1/0272; A61M 1/3693
See application file for complete search history.

(56) References Cited

U.S. PATENT DOCUMENTS

| 4,767,397 | A | 8/1988 | Hohenberg et al. |
| 5,180,504 | A | 1/1993 | Johnson et al. |

(Continued)

FOREIGN PATENT DOCUMENTS

| JP | 201150579 A | 3/2011 |
| WO | 9944718 A1 | 9/1999 |

OTHER PUBLICATIONS

International Searching Authority; International Search Report, PCT/JP2016/058613, dated May 30, 2016, 2 pages, English translation.

*Primary Examiner* — Timothy C Cleveland
(74) *Attorney, Agent, or Firm* — Terumo BCT, Inc IP Law Department

(57) ABSTRACT

A centrifuge (70) is provided with a cup (80) configured to house a blood bag system (10a) and centrifugally separates blood in the blood bag system (10a) by rotating the cup (80). The cup (80) has a segment holding section (86) capable of holding a plurality of segment tubes (44a), aligned in a parallel state by being folded at a sealing portion (44b) of an outlet-side tube (44), along a direction in which a centrifugal force acts during centrifugal processing or a direction inclined with respect to the direction in which the centrifugal force acts.

3 Claims, 7 Drawing Sheets

(51) Int. Cl.
*A61M 1/02* (2006.01)
*A61M 1/36* (2006.01)

(52) U.S. Cl.
CPC ......... *A61M 1/3693* (2013.01); *B04B 5/0421* (2013.01); *B04B 5/0428* (2013.01); *B04B 2005/0435* (2013.01)

(56) References Cited

U.S. PATENT DOCUMENTS

2002/0046967 A1* 4/2002 Romanauskas ..... A61M 1/0209
                                                              210/360.1
2004/0182734 A1   9/2004  Demay et al.
2008/0058755 A1   3/2008  Yee
2009/0286221 A1  11/2009  Klip et al.

* cited by examiner

CENTRIFUGE AND SEGMENT HOLDER

TECHNICAL FIELD

The present invention relates to a centrifuge for blood and a segment holding section.

BACKGROUND ART

Recently, blood component transfusion in which components of blood (whole blood) obtained by blood donation or the like are separated and only the components required by a patient are provided has been conducted in blood transfusion. According to the blood component transfusion, it is possible to alleviate a burden on the patient's circulatory system and other side effects, and effective utilization of the donated blood is achieved.

Blood (whole blood) obtained from blood donation or blood components prepared from the whole blood are separated into a plurality of layers in a blood bag by centrifugation. For example, when residual components (white-cell-poor platelet-poor blood) obtained by removing white blood cells and platelets from whole blood are divided into plasma and red blood cells (concentrated red blood cells) and collected into different bags, the components are first divided into a plasma layer as a supernatant component and a layer of the red blood cells (concentrated red blood cells) as a sedimentary component by centrifugation (a centrifugation step). Thereafter, the plasma is transferred to a plasma bag via a tube connected to the blood bag so as to leave the concentrated red blood cells in the blood bag (a separation transfer step). Next, a red blood cell storage solution housed in a liquid medicine bag transferred into the blood bag via the tube such that the redblood cell storage solution is added to the concentrated red blood cells (an addition step). Incidentally, a centrifuge that performs the above-described centrifugation step and separation transfer step is disclosed, for example, in U.S. Pat. No. 6,910,998.

SUMMARY OF INVENTION

Technical Problem

Meanwhile, there is a case where confirmation (quality confirmation) on whether or not a collected blood meets a predetermined quality standard is performed in a product manufacturing step depending on a manufacturer of a blood product. In order to perform such quality confirmation, a plurality of segment tubes are formed by welding and sealing a plurality of portions spaced apart from each other in a longitudinal direction in the tube connected to the blood bag by a tube sealer or the like after transferring the blood (white-cell-poor platelet-poor blood) into the blood bag. The plurality of segment tubes are mounted to the centrifuge together with the blood bag. Blood in each segment tube is separated into red blood cells (red blood cell layer) and plasma (plasma layer) by centrifugal processing.

The quality confirmation is performed by viewing the red blood cell layer inside each segment tube after the centrifugal processing and visually determining whether a length of the red blood cell layer is a predetermined length or longer. Accordingly, it is required that a separation plane, which is a boundary between the red blood cells and the plasma, is cleanly formed in each segment tube (the plasma and the red blood cells are aligned in series along a length direction of the segment tube) in order to perform the above-described quality confirmation. However, there is a case where the blood inside each segment tube is not cleanly separated unless an attitude (arrangement angle) of each segment tube in the centrifuge is appropriate. In such a case, it is difficult to perform the quality confirmation through visual determination.

The present invention has been made in view of these problems, and an object thereof is to provide a centrifuge and a segment holding section capable of cleanly separating blood in each segment tube of a blood bag system.

Solution to Problem

In order to achieve the above-described object, a centrifuge is provided with a cup configured to house a blood bag system having a bag capable of housing blood containing plural types of blood components and centrifugally separates blood in the blood bag system by rotating the cup housing the blood bag system. The blood bag system includes a tube connected to the bag and the tube is configured such that a plurality of segment tubes having cavities independent from each other by being sealed by a plurality of portions spaced apart from each other in an extending direction of the tube. The cup has a segment holding section capable of holding the plurality of segment tubes, aligned in a parallel state by folding the tube at a plurality of sealing portions, along a direction in which a centrifugal force acts during centrifugal processing or a direction inclined with respect to the direction in which the centrifugal force acts.

According to the centrifuge of the present invention configured as described above, the plurality of segment tubes are held in an appropriate direction with respect to the direction in which the centrifugal force acts during the centrifugal processing, and thus, it is possible to cleanly separate the blood in the respective segment tubes into a plurality of layers. Therefore, it is possible to perform quality confirmation by visually determining the blood in the segment tube after the centrifugal processing.

In the above-described centrifuge, the cup may include a cup main body having a bag housing section and the segment holding section may be configured to be attachable and detachable to and from the cup main body.

With this configuration, it is possible to maintain a separation plane of blood inside each segment even if the tube extending from the bag is hung down by keeping the plurality of segment tubes to be held in the segment holding section even after the centrifugally processed blood bag system is taken out of the centrifuge. Therefore, it is possible to perform the quality confirmation through visual determination without any trouble. In addition, it is possible to shorten mounting time by setting the plurality of segments in the folded state to the segment holding section before mounting the blood bag system to the centrifuge.

In the above-described centrifuge, the segment holding section may include a reference section configured to determine whether a length of a blood cell layer in the segment tube after the centrifugal processing is a predetermined length or longer.

With this configuration, it is possible to easily perform the quality confirmation through visual determination by referring to the reference section.

In the above-described centrifuge, the segment holding section may include a hollow cylindrical holding section main body made of a transparent material and the reference section may be provided on a peripheral wall portion of the holding section main body.

With this configuration, it is possible to more quickly and easily perform the quality confirmation through visual determination by referring to the reference section while viewing the blood cell layer inside the segment tube, through the transparent holding section main body, from the outside of the segment holding section.

In addition, the present invention relates to a segment holding section that is arranged in a centrifuge which is provided with a cup configured to house a blood bag system having a bag capable of housing blood containing plural types of blood components and centrifugally separates blood in the blood bag system by rotating the cup housing the blood bag system. The blood bag system includes a tube connected to the bag and the tube is configured such that a plurality of segment tubes having cavities independent from each other by being sealed by a plurality of portions spaced apart from each other in an extending direction of the tube. The cup is capable of holding the plurality of segment tubes, aligned in a parallel state by folding the tube at a plurality of sealing portions, along a direction in which a centrifugal force acts during centrifugal processing or a direction inclined with respect to the direction in which the centrifugal force acts.

In the above-described segment holding section, the cup may be configured to include a cup main body having a bag housing section so as to be attachable and detachable to and from the cup main body.

The above-described segment holding section may include a reference section configured to determine whether a length of a blood cell layer in the segment tube after the centrifugal processing is a predetermined length or longer.

The above-described segment holding section may include a hollow cylindrical holding section main body made of a transparent material.

According to the centrifuge and the segment holding section of the present invention, it is possible to cleanly separate the blood in the respective segment tubes in the blood bag system.

DESCRIPTION OF EMBODIMENTS

Figure 1:
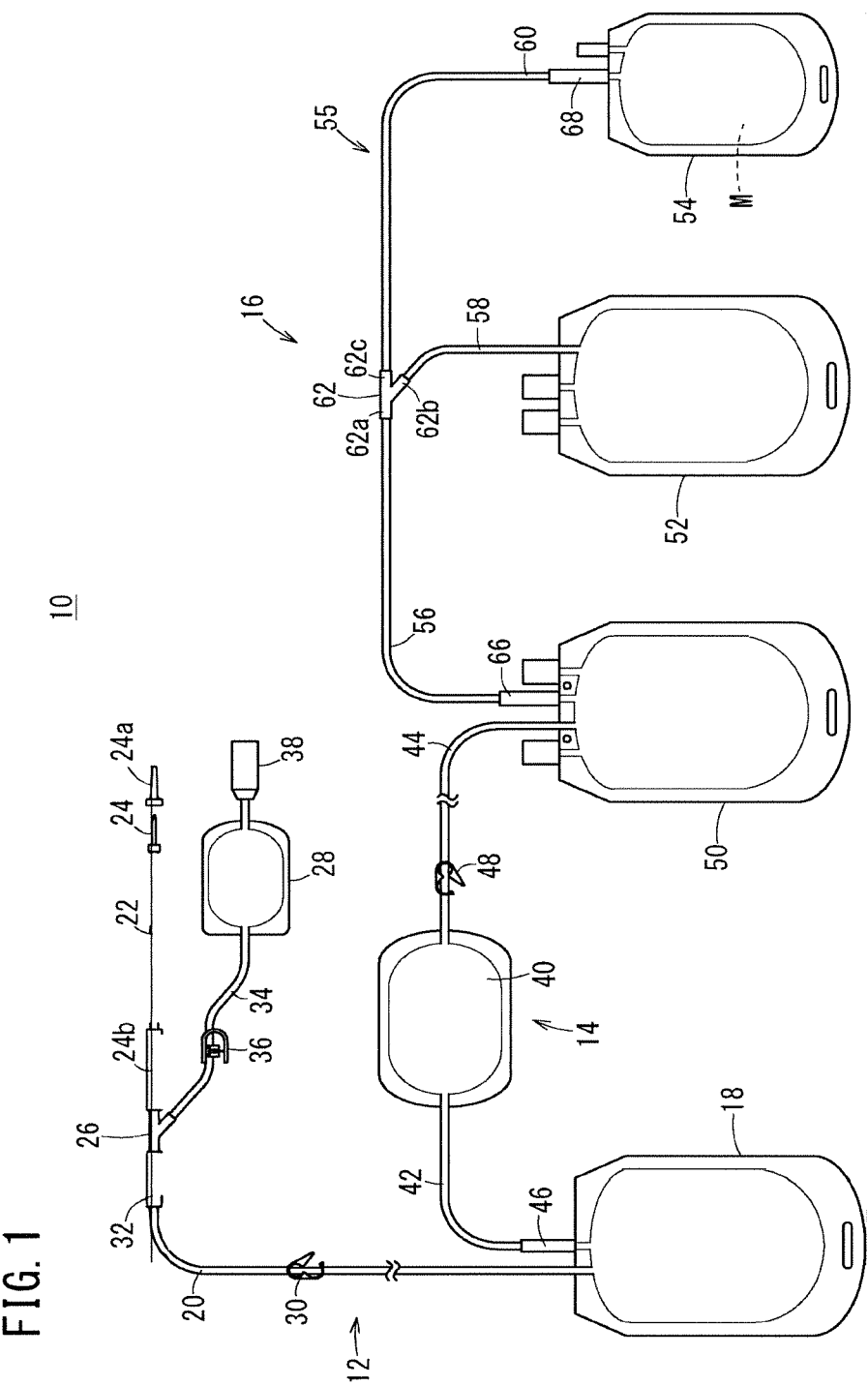
FIG. 1 is an overall schematic view of a blood bag system.

Hereinafter, preferred embodiments of a centrifuge and a segment holding section according to the present invention will be described with reference to the accompanying drawings.

A blood bag system 10 illustrated in FIG. 1 will be described before describing a configuration of a centrifuge 70 (FIG. 3 and the like) according to an embodiment of the present invention. This blood bag system 10 is configured to centrifugally separate blood containing a plurality of components into the plurality of components having different specific gravities (for example, two components of a light specific gravity component and a heavy specific gravity component) and house and store the respective components separately into different bags. More specifically, the blood bag system 10 is configured to centrifugally separate blood (white-cell-poor platelet-poor blood), obtained by removing white blood cells and platelets from whole blood, into two components of plasma and concentrated red blood cells and to house and store the plasma and the concentrated red blood cells separately in different bags.

The blood bag system 10 includes a blood collection unit 12 to collect blood (whole blood) from a donor, a preprocessing unit 14 to remove a predetermined blood component from the whole blood, and a separation processing unit 16 to centrifugally separate residual blood components, obtained by removing the predetermined component, into a plurality of blood components and house (store) the respective components in the different bags.

The blood collection unit 12 includes a blood collection bag 18, blood collection tubes 20 and 22, a blood collection needle 24, a branching connector 26, and an initial flow blood bag 28.

The blood collection bag 18 is a soft bag configured to house (store) the blood (whole blood) collected from the donor. Preferably, an anticoagulant is placed in the blood collection bag 18 in advance.

A clamp 30, which closes and opens a flow path of the blood collection tube 20, is provided in the blood collection tube 20 whose one end is connected to the blood collection bag 18. The branching connector 26 is connected to the other end of the blood collection tube 20 via a sealing member 32. Although the flow path is closed in an initial state of the sealing member 32, it is configured such that the flow path is opened by performing a breaking operation of the sealing member 32.

The blood collection tube 22 has one end connected to the branching connector 26 and the other end connected to the blood collection needle 24. A cap 24a is mounted to the blood collection needle 24 before use. After use of the blood collection needle 24, a needle guard 24b is moved along the blood collection tube 22 so that the blood collection needle 24 is covered by the needle guard 24b.

A clamp 36, which closes and opens a flow path of a branching tube 34, is provided in the branching tube 34 whose one end is connected to the branching connector 26. The initial flow blood bag 28 is connected to the other end of the branching tube 34. A sampling port 38 is connected to the initial flow blood bag 28. Incidentally, a direction or arrangement of the branching connector 26 is not limited to the configuration illustrated in FIG. 1 and can be appropriately changed.

The preprocessing unit 14 includes a filter 40 to remove a predetermined cell, an inlet-side tube 42 having one end connected to the blood collection bag 18 and the other end connected to an inlet of the filter 40, and an outlet-side tube 44 having one end connected to an outlet of the filter 40 and the other end connected to the separation processing unit 16.

In the present embodiment, the filter 40 is configured as a white blood cell removal filter. As such a white blood cell removal filter, it is possible to use a filter having a structure in which a liquid-passing porous body having numerous micropores communicating from one face to the other face thereof is housed in a bag-shaped housing formed using a flexible resin sheet. In the present embodiment, the filter 40 is configured to be capable of supplementing platelets as well.

A sealing member 46 having the same configuration and function as the above-described sealing member 32 is provided at an end portion of the inlet-side tube 42 on the blood collection bag 18 side. A clamp 48, which closes and opens a flow path of the outlet-side tube 44, is provided in the outlet-side tube 44.

The separation processing unit 16 includes a parent bag 50 to house (store) blood, obtained after removing the predetermined cell by the filter 40, a child bag 52 to house and store a supernatant component, obtained by centrifugally separating the blood in the parent bag 50, a liquid medicine bag 54 to house a red blood cell storage solution M (hereinafter, referred to as "storage solution M"), which is an additive solution, and a transfer line 55 connected to the parent bag 50, the child bag 52, and the liquid medicine bag 54.

The parent bag 50 functions as a bag for housing (storing) the blood obtained after removing the predetermined cell by the filter 40 and as a bag for storing a sedimentary component (concentrated red blood cell) obtained by centrifugally separating the blood component.

The transfer line 55 includes a first tube 56 connected to the parent bag 50, a second tube 58 connected to the child bag 52, a third tube 60 connected to the liquid medicine bag 54, and a branching connector 62 (branching portion) connected to the first to third tubes 56, 58, and 60.

A sealing member 66 having the same configuration and function as the above-described sealing member 32 is provided at one end portion (end portion on the parent bag 50 side) of the first tube 56, thereby preventing the blood components in the parent bag 50 from being transferred to the other bags until the breaking operation is performed.

The other end portion of the first tube 56 is connected to a first port 62*a* of the branching connector 62. One end of the second tube 58 is connected to a second port 62*b* of the branching connector 62. One end of the third tube 60 is connected to a third port 62*c* of the branching connector 62.

For example, an MAP solution, an SAGM solution, OPTISOL, or the like is used as the storage solution M housed in the liquid medicine bag 54. A sealing member 68 having the same configuration and function as the above-described sealing member 32 is provided at an end portion of the third tube 60 on the liquid medicine bag 54 side, thereby preventing the storage solution M in the liquid medicine bag 54 from being transferred to the other bags.

The respective tubes in the blood bag system 10 are transparent and flexible tubes made of resin.

It is possible to perform a process of collecting the blood (whole blood) from the donor using the blood bag system 10 illustrated in FIG. 1, removing the white cells and the platelets from the collected blood, separating the residual components (white-cell-poor platelet-poor blood) into two layers of the plasma and the concentrated red blood cells, and storing the separated components separately into the bags according to the following procedure, for example.

First, a blood collection step of puncturing a skin of the donor with the blood collection needle 24 and collecting the blood from the donor is performed. In the blood collection step, an initial flow of the blood (initial blood flow) from the donor is housed in the initial flow blood bag 28 by a predetermined amount prior to the collection of blood into the blood collection bag 18. In this case, the clamp 36 is turned into an open state while keeping the sealing member 32 in a closed state (initial state). In this manner, the inflow of the initial blood flow into the blood collection tube 20 side, that is, the blood collection bag 18 side is blocked, and it is possible to introduce the initial blood flow can be introduced into the initial flow blood bag 28 via the blood collection tube 22, the branching connector 26, and the branching tube 34.

Next, a blood sampling tube (not illustrated) is mounted to the sampling port 38 to collect the initial blood flow in the blood sampling tube. The collected initial blood flow is used as blood for examination. Incidentally, a portion from the branching connector 26 to the sampling port 38 may be omitted depending on the application.

After ending the collection of the initial blood flow, the branching tube 34 is closed with the clamp 36, and the breaking operation is performed on the sealing member 32 to open the flow path of the blood collection tube 20. At this time, when the clamp 30 is kept in an open state, the blood from the donor flows into the blood collection bag 18 via the blood collection tube 22 and the blood collection tube 20 in order.

When a predetermined amount of blood is collected and stored in the blood collection bag 18, the blood collection tube 20 is closed by the clamp 30 such that the blood in the blood collection bag 18 does not flow out. Further, the blood collection tube 20 is welded and sealed by a tube sealer or the like, and then, the blood collection tube 20 is cut at this sealed portion.

Next, the blood collection bag 18 is set to a relatively upper position, the parent bag 50 is set to a relatively lower position, and the filter 40 is arranged at an intermediate position therebetween, and then, the breaking operation is performed on the sealing member 46 to open the flow path of the inlet-side tube 42. Accordingly, the whole blood in the blood collection bag 18 flows into the filter 40 via the inlet-side tube 42, and the white blood cells and the platelets are removed in the process of passing through the filter 40. The blood from which the white blood cells and the platelets have been removed flows into the parent bag 50 via the outlet-side tube 44.

Figure 2:
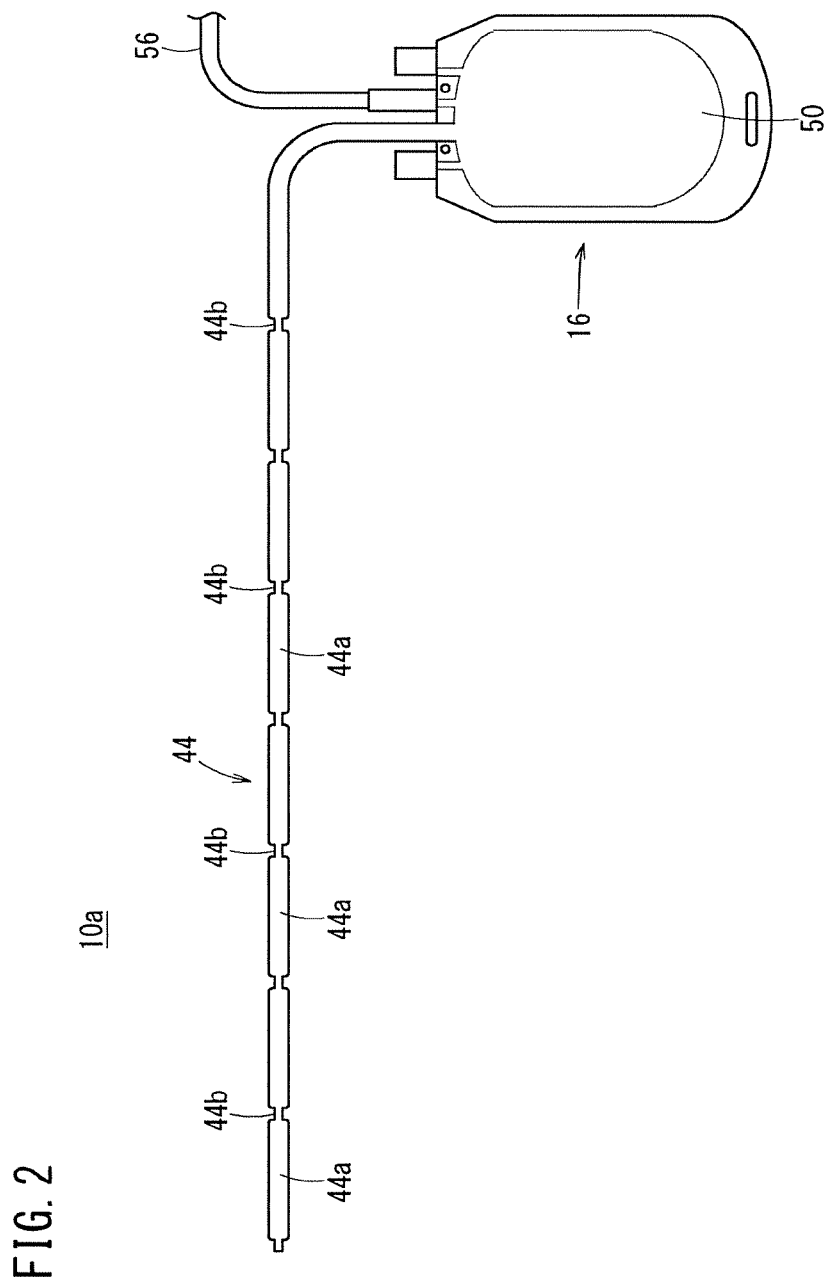
FIG. 2 is an explanatory view of a segment tube.

Thereafter, the outlet-side tube 44 is welded and sealed at a position on the downstream side of the clamp 48 by the tube sealer or the like, and then, the outlet-side tube 44 is cut at this sealed portion. In addition, a plurality of portions spaced apart from each other in an extending direction are welded and sealed by the tube sealer or the like in the outlet-side tube 44 connected to the parent bag 50 to form a plurality (seven in the illustrated example) of segment tubes 44*a* as illustrated in FIG. 2 in order to perform the quality confirmation after the centrifugal processing.

The plurality of segment tubes 44*a* have cavities (liquid chambers), which are independent from each other, and are in a state where the blood after being filtered by the filter 40 is enclosed in each of the cavities. The respective segment tubes 44*a* have the same length, and are formed to have a length of, for example, 60 to 80 mm.

Figure 3:
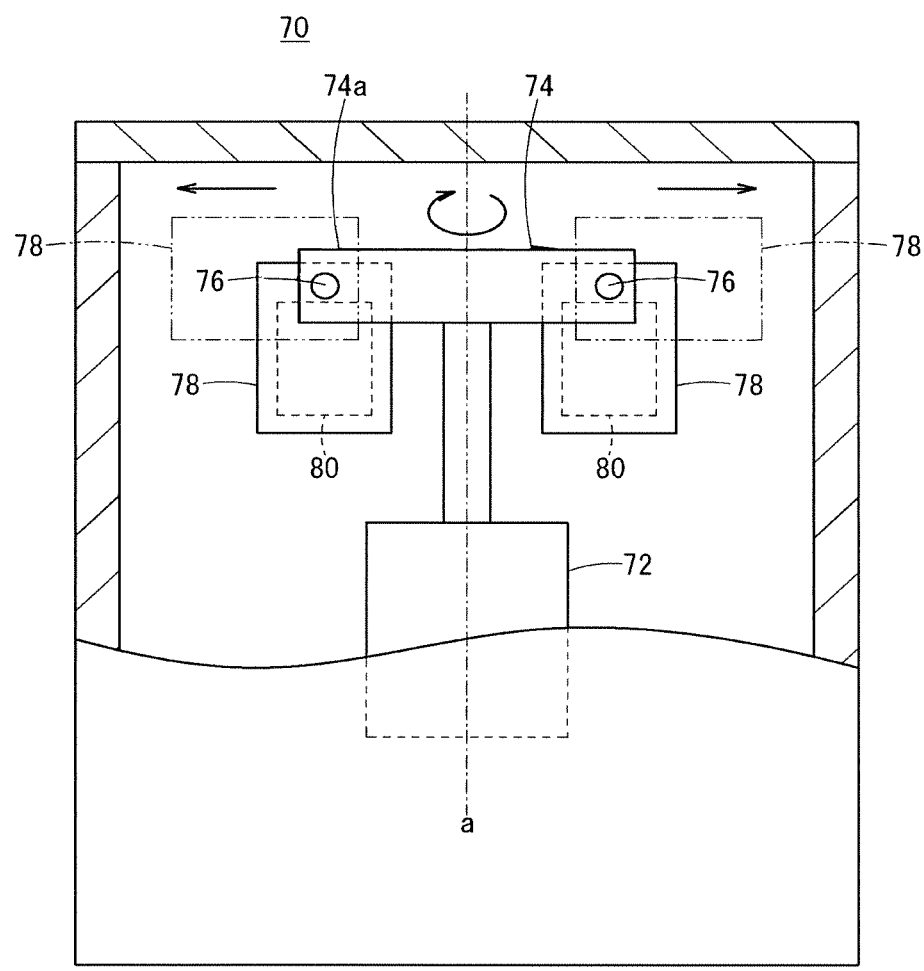
FIG. 3 is a schematic configuration diagram of a centrifuge according to an embodiment of the present invention.

Next, the separation processing unit 16 and the outlet-side tube 44 (the outlet-side tube 44 forming the segment tube 44*a*) are mounted to the centrifuge 70 illustrated in FIG. 3 in order to execute a centrifugation step (centrifugal processing) of separating the blood collected in the parent bag 50 into the plasma and the concentrated red blood cells. Hereinafter, a portion of the blood bag system 10 that is a target of the centrifugal processing, that is, the separation processing unit 16 and the outlet-side tube 44 including the parent bag 50 will be referred to as a "blood bag system 10*a*" for the convenience of description.

The centrifuge 70 according to the present embodiment is configured as follows. The centrifuge 70 includes a motor 72 which is a drive source, a rotor 74 which is driven to rotate about a rotation axis a by the motor 72, a plurality of buckets 78 suspended and supported by an arm 74*a* of the rotor 74 via a pin 76, a cup 80 which is capable of housing the blood bag system 10 and is loaded in each of the buckets 78, and a housing 82 which houses these parts.

The bucket 78 is formed in a bottomed tubular shape that is opened upward. The bucket 78 is rotatably supported by the arm 74a of the rotor 74 via the pin 76 at an upper part thereof. Therefore, the bucket 78 is directed vertically (a vertical attitude) as indicated by the solid line in FIG. 3 when the rotor 74 stops (does not rotate). On the other hand, the bucket 78 is directed laterally (a horizontal attitude) as indicated by the virtual line in FIG. 3 under action of a centrifugal force when the rotor 74 rotates.

Figure 4:
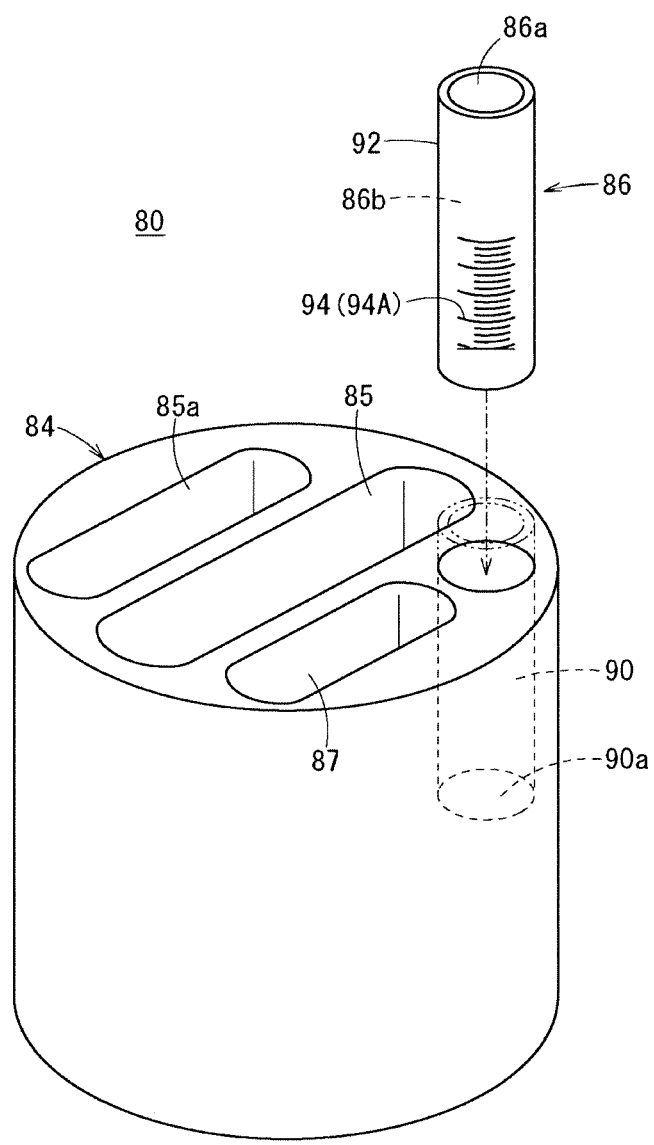
FIG. 4 is a perspective view of a cup in the centrifuge.

As illustrated in FIG. 4, the cup 80 includes a cup main body 84 having bag housing sections 85, 85a and 87 and a segment holding section 86 configured to be attachable and detachable to and from the cup main body 84.

Each of the bag housing sections 85, 85a and 87 is formed in the form of a bottomed hole that is opened upward. The bag housing section 85, which is the largest, is formed in a shape suitable for housing the parent bag 50 in the vertical direction. The bag housing section 86 is formed in a shape suitable for housing the child bag 52. The bag housing section 87 is formed in a shape suitable for housing the liquid medicine bag 54. Incidentally, only one bag housing section may be provided in the cup main body 84.

The cup main body 84 has a mounting section 90 to and from which the segment holding section 86 is attachable and detachable. In the present embodiment, the mounting section 90 is formed in the form of a bottomed hole that extends along an axial direction (height direction) of the cup main body 84 and is opened upward. The axial direction of the cup main body 84 is parallel to a direction in which the centrifugal force acts during a centrifugal operation of the centrifuge 70 (during the rotation of the rotor 74). When the segment holding section 86 is inserted into the mounting section 90, a bottom surface of the segment holding section 86 abuts on a bottom portion 90a of the mounting section 90, thereby stopping the segment holding section 86 at a predetermined position.

A protrusion to lock the segment holding section 86 may be provided on an inner wall surface forming the mounting section 90 such that the segment holding section 86 is stopped at the predetermined position by the protrusion. Incidentally, the mounting section 90 may be provided on an outer peripheral surface of the cup main body 84.

The segment holding section 86 is configured to be capable of holding the plurality of segment tubes 44a (see FIG. 5), aligned in a parallel state by folding the outlet-side tube 44 at the sealing portion 44b, in the direction in which the centrifugal force acts during the centrifugal processing in the present embodiment.

The segment holding section 86 is formed in a shape suitable for housing the plurality of segment tubes 44a aligned in the parallel state. The segment holding section 86 includes a housing chamber 86b, which is open at one end (an upper end in FIG. 5) and closed at the other end (a lower end in FIG. 5), and is formed in a hollow cylindrical shape (hollow tubular shape in FIG. 5) in the present embodiment. The plurality of segment tubes 44a are pressed against the inner peripheral surface of the segment holding section 86 by a force of the plurality of segment tubes 44a trying to spread due to an elastic force of the sealing portion 44b in a state where the plurality of segment tubes 44a aligned in the parallel state are housed in the segment holding section 86.

Dimensions of the segment holding section 86 are appropriately set such that the segment tube 44a does not protrude during the centrifugal processing, the segment tube 44a does not twist, and a separation plane 98 (see FIG. 7) of blood inside the segment tube 44a can be cleanly formed. For example, an inner diameter D (a diameter of the housing chamber 86b) of the segment holding section 86 is set to 10 to 30 mm, and preferably to 15 to 25 mm. In addition, a length L of the housing chamber 86b is set to 60 to 150 mm, and preferably to 80 to 100 mm.

Figure 5:
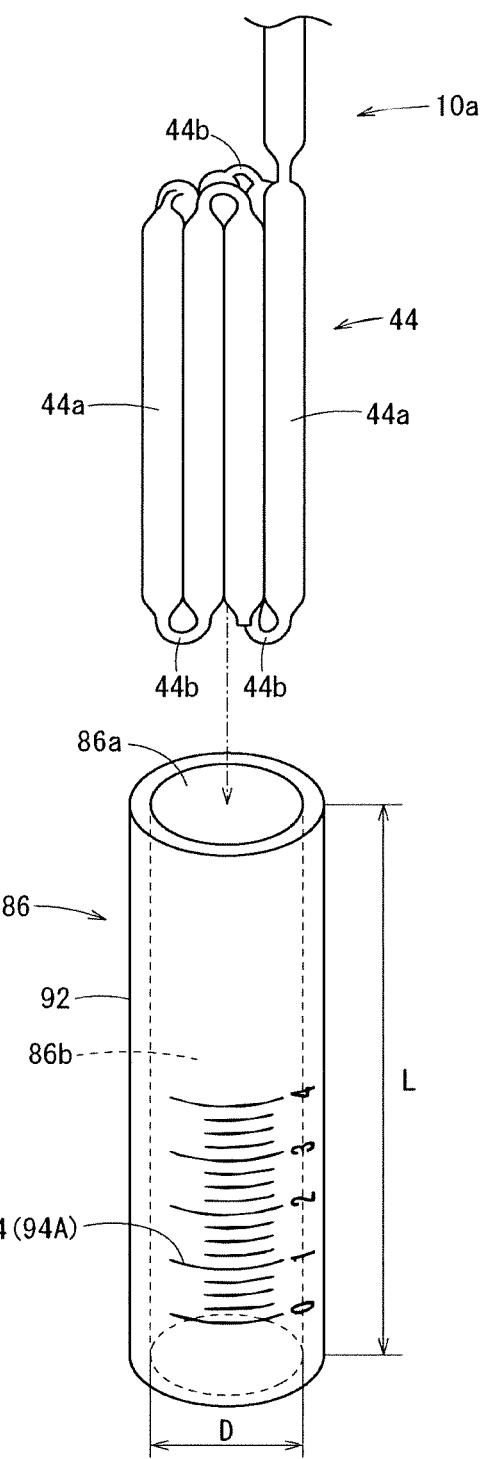
FIG. 5 is an explanatory view of a segment holding section and a plurality of segment tubes.

In FIGS. 4 and 5, the segment holding section 86 includes a hollow cylindrical holding section main body 92 made of a transparent material and a reference section 94 provided on a peripheral wall portion of the holding section main body 92.

The reference section 94 is a means for determining whether the red blood cell layer in the segment tube 44a after the centrifugal processing is a predetermined length or longer (for example, 15 mm or longer in a length direction of the segment tube 44a), and has the form of a scale section 94A having a plurality of graduation lines in FIG. 5.

Figure 6:
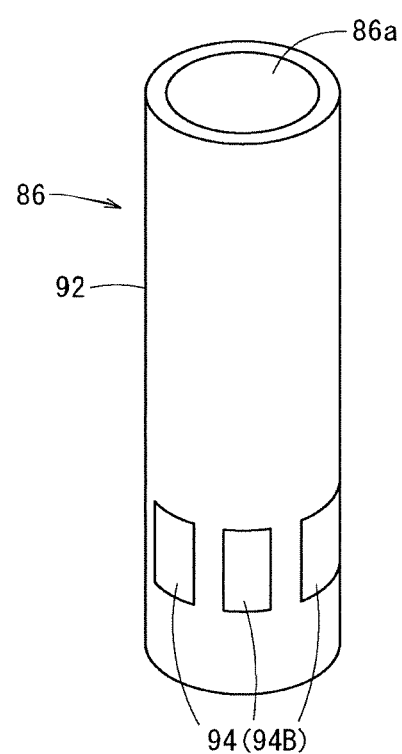
FIG. 6 is a perspective view of a segment holding section provided with a reference section according to a modified example.

As illustrated in FIG. 6, the reference section 94 provided in the segment holding section 86 may have the form of a reference marker 94B having a predetermined length (for example, 15 mm) along the length direction of the holding section main body 92. The reference marker 94B is provided at a location close to the lower end of the segment holding section 86. Only the single reference marker 94B may be provided in a circumferential direction, but a plurality of the reference markers 94B may be provided with intervals in the circumferential direction as illustrated in FIG. 6. The reference marker 94B illustrated in FIG. 6 is formed in a band shape (rectangular shape), but may be formed in a line shape.

The above-described blood bag system 10a (in the state where the blood after being filtered by the filter 40 is housed in the parent bag 50 and the blood is enclosed in the plurality of segment tubes 44a of the outlet-side tube 44 connected to the parent bag 50) is mounted to the centrifuge 70 configured as described above.

In this case, the outlet-side tube 44 is first alternately folded at the sealing portion 44b to bundle the plurality of segment tubes 44a in the parallel state as illustrated in FIG. 5. Further, the plurality of segment tubes 44a in the bundled state is inserted into the inside of the segment holding section 86 through an opening portion 86a of the segment holding section 86. Accordingly, the respective segment tubes 44a are held in the inside (the housing chamber 86b) of the segment holding section 86 in the state of being directed in the length direction of the segment holding section 86.

Next, the parent bag 50, the child bag 52, and the liquid medicine bag 54 are inserted into the bag housing sections 85, 85a, and 87 of the cup main body 84, respectively, and the segment holding section 86 holding the plurality of segment tubes 44a is mounted to the mounting section 90 of the cup main body 84. Further, the cup 80 in this state is loaded in the bucket 78 of the centrifuge 70 in a stop state. Incidentally, the number of bag housing sections provided in the cup main body 84 is arbitrary, and any bag housing section in which any bag is housed may be arbitrarily determined.

Figure 7:
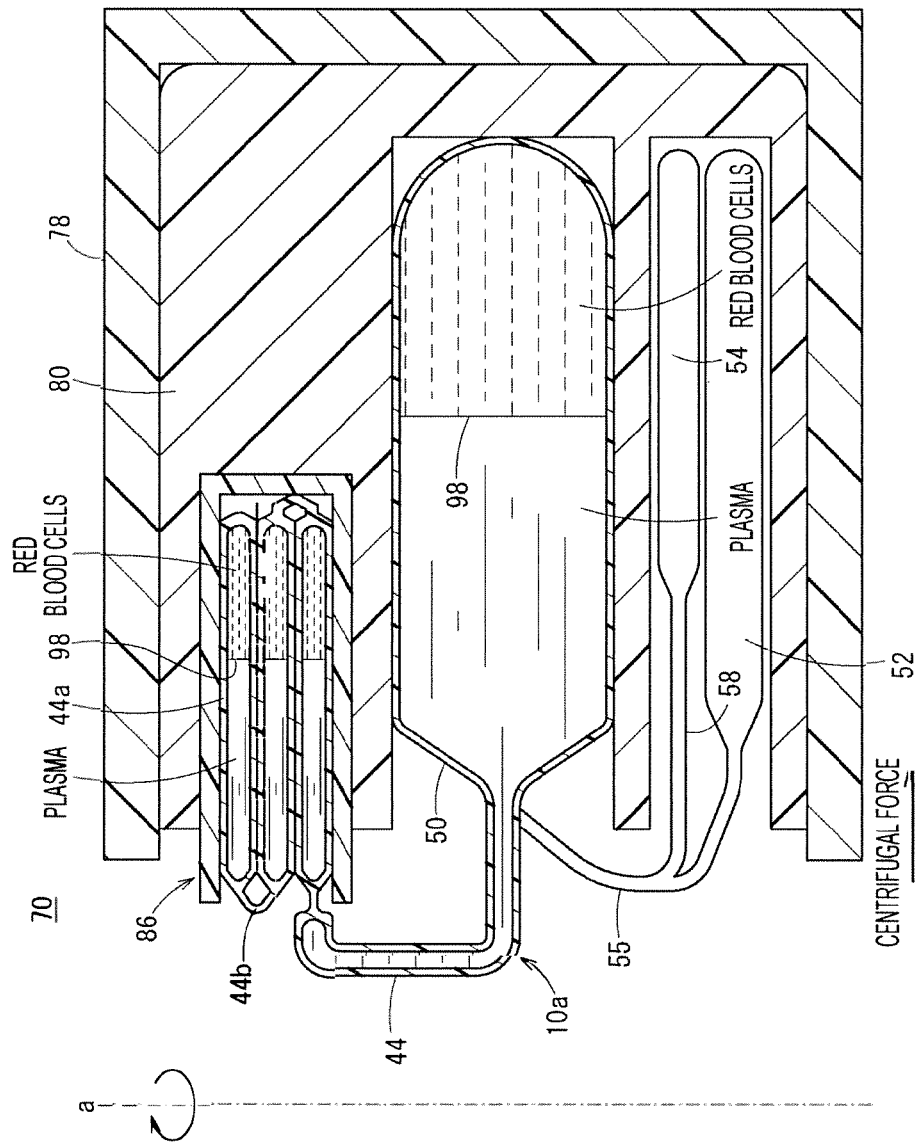
FIG. 7 is an explanatory view at the time of centrifugal processing using the centrifuge.

Next, the rotor 74 is rotated about the rotation axis a under the drove action of the motor 72 in the centrifuge 70. FIG. 7 schematically illustrates a state of the centrifuge 70 at this time. As illustrated in FIG. 7, the bucket 78 swings in a direction (horizontal direction) perpendicular to the rotation axis a together with the cup 80 loaded in the bucket 78 by the centrifugal force while rotating about the rotation axis a.

Along with the rotation about the rotation axis a, the blood in the parent bag 50 housed in the cup 80 and the blood in the respective segment tubes 44a held in the segment holding section 86 receive the centrifugal force in a bottom direction of the cup 80. Accordingly, the blood is centrifugally separated into the plasma of the light specific gravity component and the red blood cells (concentrated red blood cells) of the heavy specific gravity component due to a difference in specific gravity. The separation plane 98 is formed at a boundary between the plasma and the red blood cells. After predetermined centrifugal separation is performed, the centrifuge 70 decelerates and stops the motor 72.

Thereafter, the blood bag system 10a after the centrifugal processing is removed from the centrifuge 70. Specifically, first, the cup 80 housing the blood bag system 10a is extracted from the bucket 78 and taken out of the centrifuge 70. Next, the segment holding section 86 is detached (extracted) from the mounting section 90 of the cup main body 84 while holding the plurality of segment tubes 44a in the segment holding section 86. Accordingly, the state where the plurality of segment tubes 44a are bundled in the parallel state is held even after the blood bag system 10a is taken out of the centrifuge 70.

Next, a separation transfer step of transferring the plasma from the parent bag 50 to the child bag 52 via the transfer line 56 to leave the red blood cells in the parent bag 50 is executed. After end of the separation transfer step, the second tube 58 is welded and sealed by the tube sealer or the like, and the child bag 52 is cut off by cutting the sealing portion. Incidentally, the centrifuge 70 of the present embodiment may be configured to automatically perform not only the above-described centrifugation step but also the separation transfer step.

Next, an addition step of adding the storage solution M to the red blood cells (concentrated red blood cells) in the parent bag 50 is executed. Specifically, the liquid medicine bag 54 is positioned relatively upward and the parent bag 50 is positioned relatively downward such that the storage solution M is transferred from the liquid medicine bag 54 to the parent bag 50 due to a height difference via the transfer line 55.

Meanwhile, whether the length of the red blood cell layer in each of the segment tubes 44a is the predetermined length or longer is visually determined after the centrifugal processing of the blood bag system 10a performed by the centrifuge 70 in order for the quality confirmation of the collected blood. In order to properly perform the quality confirmation through such visual determination, it is required that the blood is cleanly separated into the plasma and the red blood cells (the plasma and the red blood cells are aligned in series in the length direction of the segment tube 44a) in all the segment tubes 44a.

Since the plurality of segment tubes 44a are held by the segment holding sections 86 along the direction in which the centrifugal force acts during the centrifugal processing in the centrifuge 70 of the present embodiment, it is possible to cleanly separate the blood in each of the segment tubes 44a into the plasma and the red blood cells as illustrated in FIG. 7. Therefore, it is possible to perform the quality confirmation by visually determining the blood in the segment tube 44a after the centrifugal processing.

In this case, the holding section main body 92 made of the transparent material is provided with the reference section 94 in the segment holding section 86 (FIGS. 4 and 5). Thus, it is possible to determine whether the length of the red blood cell layer is the predetermined length or longer by referring to the reference section 94 while viewing the red blood cell layer inside each of the segment tubes 44a, through the transparent holding section main body 92, from the outside of the segment holding section 86. Specifically, when the reference section 94 has the form of the scale section 94A as illustrated in FIG. 5, it is possible to perform the above-described determination based on whether the length of the red blood cell layer measured with reference to the scale section 94A is the predetermined length or longer. When the reference section 94 has the form of the reference marker 94B as illustrated in FIG. 6, it is possible to perform the above-described determination based on whether the length of the red blood cell layer is longer than the reference marker 94B.

Incidentally, the segment holding section 86 may hold the plurality of segment tubes 44a aligned in the parallel state by folding the outlet-side tube 44 at the sealing portion 44b in a direction inclined with respect to the direction in which the centrifugal force acts during the centrifugal processing by being mounted so as to be inclined with respect to the axial direction of the cup main body 84.

The segment holding section 86 may be configured not be removed from the cup main body 84, which is different from the present embodiment. In such a configuration, the plurality of segment tubes 44a hangs down in series (extends in an up and down direction) in the case of hanging the outlet-side tube 44, which extends from the parent bag 50, after taking out the blood bag system 10a subjected to the centrifugal processing from the centrifuge 70. At this time, the red blood cells as the heavy specific gravity component are present in the lower part of one in two of the plurality of segment tubes 44a, and the plasma as the light specific gravity component is present in the upper part. Thus, when the hanging state of the outlet-side tube 44 continues, the plasma and the red blood cells are gradually mixed by gravity and the separation plane 98 disappears.

On the other hand, since the segment holding section 86 is configured to be attachable and detachable to and from the cup main body 84, it is possible to maintain the separation plane 98 of blood in each of the segment tubes 44a in the present embodiment. That is, the plurality of segment tubes 44a are held in the segment holding section 86 even after taking out the blood bag system 10a subjected to the centrifugal processing from the centrifuge 70. In this manner, even when the outlet-side tube 44 extending from the parent bag 50 is hung and left to stand, the red blood cells as the heavy specific gravity component are present in the lower part and the plasma as the light specific gravity component is present in the upper part in each of the segment tubes 44a held by the segment holding section 86. Thus, the separation plane 98 does not disappear due to mixing of the plasma and the red blood cells caused by gravity. Therefore, it is possible to perform the quality confirmation through visual determination without any trouble.

Further, it is possible to shorten the mounting time of the blood bag system 10a by setting the plurality of segment tubes 44a to the segment holding section 86 before mounting the blood bag system 10a to the centrifuge 70 in the present embodiment.

Since the segment holding section 86 includes the reference section 94 configured to determine whether the length of the red blood layer in the segment tube 44a after the centrifugal processing is the predetermined length or longer, it is possible to easily perform the quality confirmation through visual determination in the present embodiment. In particular, the reference section 94 is provided on the peripheral wall portion of the hollow cylindrical holding section main body 92 made of the transparent material. With this configuration, it is possible to more quickly and easily perform the quality confirmation through visual determination by referring to the reference section 94 while viewing the blood cell layer inside the segment tube 44a, through the transparent holding section main body 92, from the outside of the segment holding section 86.

Although the present invention has been described with the preferred embodiments as above, it is obvious that the present invention is not limited to the above-described embodiments, and various modifications can be made within a scope not departing from a gist of the present invention.

The invention claimed is:

1. A method of processing blood samples in a centrifuge, the centrifuge comprising a cup configured to house a blood bag system to be rotated by the centrifuge, said blood bag system comprising a bag capable of housing blood comprised of a plurality of blood components, and a tube connected to the bag, the method comprising introducing blood into the tube, forming the tube into a plurality of tube segments separated by sealing portions, each tube segment having a length, folding the tube at said sealing portions, holding the plurality of tube segments with said lengths aligned in a parallel state, inserting the tube segments into a tube segment holding section in said cup, holding said lengths of said tube segments in a direction in which a centrifugal force acts during centrifugal processing or a direction inclined with respect to the direction in which the centrifugal force acts, and separating blood in said tube segments into blood components by centrifugation.

2. The method according to claim 1, wherein the cup includes a cup main body having a bag housing section, the method further comprising attaching the tube segment holding section to the cup main body.

3. The method according to claim 2, wherein the tube segment holding section includes a reference section and the method further comprises determining whether a length of a blood cell layer in a tube segment after the centrifugal processing is a predetermined length or longer using said reference section.

* * * * *